US012678269B2

(12) United States Patent
Rmaile et al.

(10) Patent No.: US 12,678,269 B2
(45) Date of Patent: Jul. 14, 2026

(54) MOUTHPIECE FOR AN ORAL CARE DEVICE

(71) Applicant: KONINKLIJKE PHILIPS N.V., Eindhoven (NL)

(72) Inventors: Amir Hussein Rmaile, Eindhoven (NL); Lutz Christian Gerhardt, Eindhoven (NL); Mark Thomas Johnson, Arendonk (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 120 days.

(21) Appl. No.: 18/286,100

(22) PCT Filed: Apr. 6, 2022

(86) PCT No.: PCT/EP2022/059040
§ 371 (c)(1),
(2) Date: Oct. 6, 2023

(87) PCT Pub. No.: WO2022/214505
PCT Pub. Date: Oct. 13, 2022

(65) Prior Publication Data
US 2024/0180680 A1      Jun. 6, 2024

(30) Foreign Application Priority Data

Apr. 9, 2021      (EP) ..................................... 21167547

(51) Int. Cl.
*A61C 17/22*          (2006.01)
*A61B 5/00*          (2006.01)
(Continued)

(52) U.S. Cl.
CPC .............. *A61C 17/228* (2013.01); *A61B 5/11* (2013.01); *A61B 5/228* (2013.01); *A61B 5/389* (2021.01); *A61B 5/682* (2013.01)

(58) Field of Classification Search
CPC ......... A61C 17/228; A61B 5/389; A61B 5/11; A61B 5/228; A61B 5/682
See application file for complete search history.

(56) References Cited

U.S. PATENT DOCUMENTS

2011/0066066 A1      3/2011   Van Kemenade et al.
2015/0045705 A1      2/2015   Baba et al.
(Continued)

FOREIGN PATENT DOCUMENTS

CN      107080541  A      8/2017
CN      111407451  A      7/2020
(Continued)

OTHER PUBLICATIONS

International Search Report and Written Opinion Dated Sep. 23, 2022 For International Application No. PCT/EP2022/059040 Filed Apr. 6, 2022.
(Continued)

*Primary Examiner* — Ralph A Lewis

(57) ABSTRACT

An approach for obtaining measurements of mechanical properties of a gripping performed by masticatory apparatus. A mouthpiece provides a sensing arrangement (for obtaining the measurement) and one or more mouth contacting elements for protecting, cleaning or treating teeth/gums. In this way, measurements indicative of potential abnormalities or physiological dysfunction in the masticatory apparatus can be obtained using a mouthpiece that has a secondary function of protecting, cleaning and/or treating elements of the mouth.

12 Claims, 2 Drawing Sheets

(51) Int. Cl.

| | | |
|---|---|---|
| *A61B 5/11* | (2006.01) | |
| *A61B 5/22* | (2006.01) | |
| *A61B 5/389* | (2021.01) | |

(56) References Cited

U.S. PATENT DOCUMENTS

| | | | |
|---|---|---|---|
| 2018/0000565 A1* | 1/2018 | Shanjani | ............... A61C 19/04 |
| 2019/0117339 A1 | 4/2019 | Bolzan | |
| 2020/0037740 A1* | 2/2020 | Nguyen | ............. A46B 15/0012 |
| 2020/0345536 A1* | 11/2020 | Letizia | ................. A61B 5/4557 |
| 2021/0077020 A1 | 3/2021 | Tran et al. | |

FOREIGN PATENT DOCUMENTS

| | | |
|---|---|---|
| JP | 06269468 A | 9/1994 |
| JP | 2017164328 A | 9/2017 |
| KR | 101906475 B1 | 12/2018 |
| KR | 102139071 B1 | 7/2020 |
| KR | 20210022853 A | 3/2021 |
| WO | 2008061328 A2 | 5/2008 |

OTHER PUBLICATIONS

Sanches. "Clinical Management of Oral Disorders in Breastfeeding". Jornal de Pediatria—vol. 80, No. 5; (suppl), 2004; pp. S155-S162.

National Institute of Dental and Craniofacial Research. "Prevalence of TMJD and its Signs and Symptoms". Last Reviewed Jul. 2018. https://www.nidcr.nih.gov/research/data-statistics/facial-pain/prevalence.

National Library of Medicine—National Center for Biotechnology Information. Fernanda Mara de Paiva Bertoli et al "Prevalence of diagnosed temporomandibular disorders: A cross-sectional study in Brazilian adolescents". PLoS One. 2018; 13(2): e0192254. Published online Feb. 8, 2018. doi: 10.1371/journal.pone.0192254.

National Library of Medicine—National Center for Biotechnology Information. Kashef K. AlShaban et al "Prevalence of TMJ Disorders among the Patients Attending the Dental Clinic of Ajman University of Science and Technology—Fujairah Campus, UAE". Int J Dent. 2018; 2018: 9861623.

Moghees A. Baig National Library of Medicine—National Center for Biotechnology Information. Baig MA (Oct. 2004). "Surgical enhancement of facial beauty and its psychological significance". Annals of the Royal Australasian College of Dental Surgeons. 17: 64-7. PMID 16479858.

B Palumbo et al National Library of Medicine—National Center for Biotechnology Information. Palumbo B, Cassese R, Fusetti S, Tartaro GP (2006). "Psychological aspects of orthognathic treatment". Minerva Stomatologica. 55 (1-2): 33-42. PMID 16495871.

J Stirling et al National Library of Medicine—National Center for Biotechnology Information. Stirling J, Latchford G, Morris DO, Kindelan J, Spencer RJ, Bekker HL (Jun. 2007). "Elective orthognathic treatment decision making: a survey of patient reasons and experiences". Journal of Orthodontics. 34 (2): 113-27, discussion 111. doi: 10.1179/146531207225022023. PMID 17545299.

Y H Zhou et al National Library of Medicine—National Center for Biotechnology Information. Zhou YH, Hägg U, Rabie AB (2001). "Concerns and motivations of skeletal Class III patients receiving orthodontic-surgical correction". The International Journal of Adult Orthodontics and Orthognathic Surgery. 16 (1): 7-17. PMID 11563399.

M Modig et al National Library of Medicine—National Center for Biotechnology Information. Modig M, Andersson L, Wårdh I (Feb. 2006). "Patients' perception of improvement after orthognathic surgery: pilot study". The British Journal of Oral & Maxillofacial Surgery. 44 (1): 24-7. doi:10.1016/j.bjoms.2005.07.016. PMID 16162374.

* cited by examiner

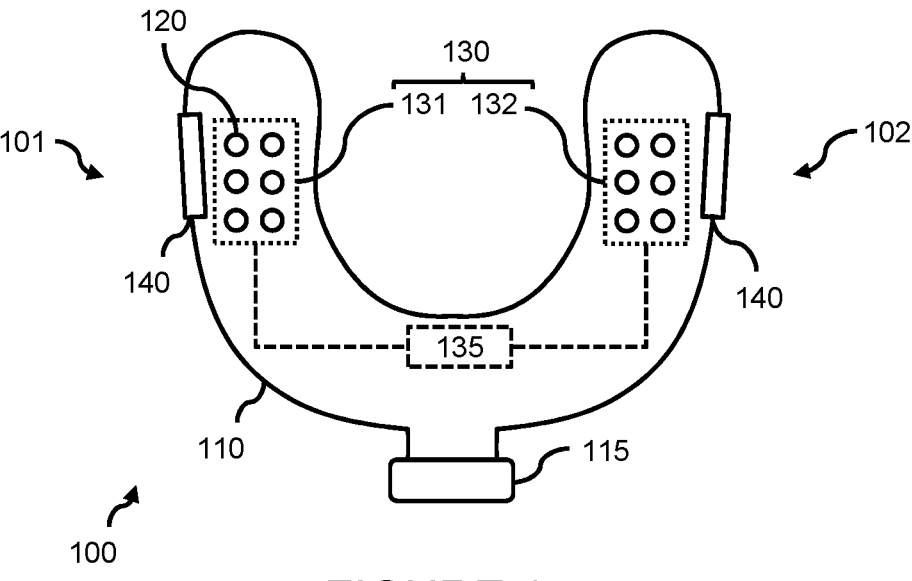
FIGURE 1
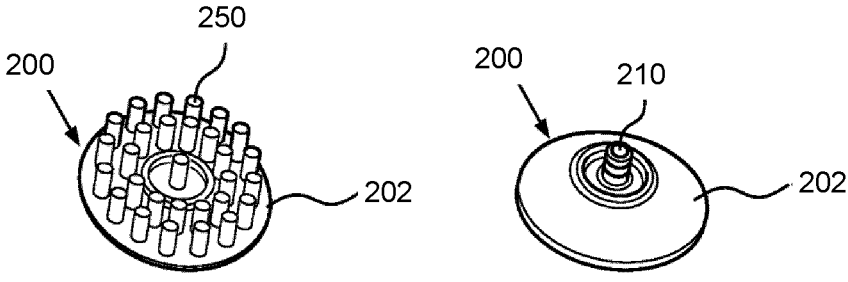
FIGURE 2
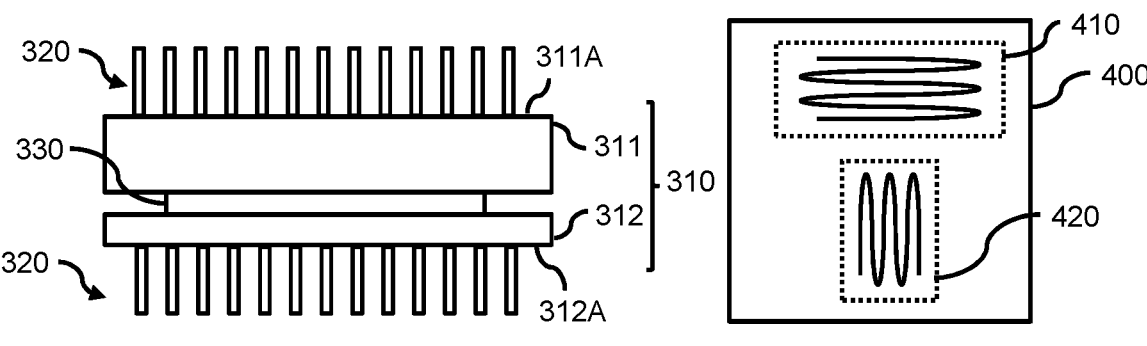
FIGURE 3
FIGURE 4

MOUTHPIECE FOR AN ORAL CARE DEVICE

This application is the U.S. National Phase application under 35 U.S.C. § 371 of International Application No. PCT/EP2022/059040, filed on Apr. 6, 2022, which claims the benefit of EP Application Serial No. 21167547.5, Filed Apr. 9, 2021. These applications are hereby incorporated by reference herein.

FIELD OF THE INVENTION

The present invention relates to the field of oral care, and in particular to mouthpieces for oral care devices.

BACKGROUND OF THE INVENTION

Dental occlusion disorders, usually resulting from jaw or masticatory apparatus abnormalities (whether dental or skeletal in nature) are quite common worldwide. These problems include (and can be caused by) malocclusion, teeth misalignment, bruxism, teeth wear, facial muscle pain or temporomandibular joint and muscle (TMJ) disorders.

Early detection of abnormal occlusal problems can prevent serious complications. Individuals with jaw or other masticatory apparatus abnormalities have both functional and aesthetic impairment. Misalignment of teeth creates difficulties in head and neck functions related to chewing, swallowing, breathing, speech articulation and lip closure/posture. Affected individuals may also experience TMJ pain and dysfunction, which negatively affect the quality of life. A proportion of affected individuals also have psychological problems.

One significant problem area involves TMJ disorders, which are usually detected too late for effective treatment. There has been an increasing recognition of the prevalence of dental occlusion disorders or masticatory apparatus disorders, such as temporomandibular joint and muscle disorders, which can be as high as 50% in some population groups. Recent studies have demonstrated that 25% of people in the United States deal with occlusal dentition induced migraine, and 25-30% have some variety of a TMJ disorder.

Unusually for chronic pain conditions, the prevalence rates of TMJ disorders are higher among younger persons. Moreover, TMJ disorders are at least twice as prevalent in women as men, and women using either supplemental estrogen or oral contraceptives are more likely to seek treatment for these conditions.

While TMJ disorders and malocclusion dysfunctions are usually only checked by a dental professional in regular check-ups, there is therefore an ongoing desire to enable self-testing in a home environment and improve the ability to identify the presence of abnormalities or physiological dysfunction in the masticatory apparatus, such as the presence of a TMJ disorder.

SUMMARY OF THE INVENTION

The invention is defined by the claims.

According to examples in accordance with an aspect of the invention, there is provided a mouthpiece. The mouthpiece comprises: a mount configured to be gripped between upper and lower jaws of a subject: one or more mouth contacting elements, each being configured to contact one or more parts of the mouth of the subject and protect, treat and/or clean the contacted one or more parts of the mouth when the mount is gripped between the upper and lower jaws: and a sensing arrangement positioned in or on the mount, wherein the sensing arrangement is configured to sense, during gripping of the mount by the upper and lower jaws of the subject, one or more measurements of mechanical properties of the gripping by the upper and lower jaws, wherein the one or more measurements of the mechanical properties are responsive to one or more abnormalities or physiological dysfunction in masticatory apparatus of the subject.

The present disclosure proposes an approach for generating data useful for identifying the presence or effects of a dental occlusion disorder (i.e. an abnormality in the jaws) of a subject. The abnormality may present in the muscles, teeth and/or joint of the jaw (i.e. in the masticatory apparatus of the subject), and may relate to a misalignment (e.g. of teeth or a movement of the jaw), an unevenness (e.g. of teeth or of a bite) and so on.

The present disclosure proposes integrating sensors with a mouthpiece that is used to brush or clean the subject's teeth, in order to gather data during a cleaning procedure. In other words, the disclosure proposes using a cleaning mouthpiece as a carrier for sensors used to gather data for occlusal analysis.

The sensing arrangement gathers data during a gripping of the mouthpiece. The gripping is a time during which the mouthpiece is held between the jaws of the subject, and may include (for instance) a period during which the subject clamps down upon the mouthpiece and/or maintains pressure on the mouthpiece and/or releases pressure from the mouthpiece. A gripping may include a "loose" grip (in which the mouthpiece is loosely held between the jaws) and a "tight" grip (in which the mouthpiece is tightly held between the jaws), as well as movement between the loose grip and the tight grip.

Any suitable mechanical property of the gripping by the upper and lower jaws may be measured. In particular, a mechanical property may be measured or sampled during a time period in which pressure is being (increasingly) applied to the mouthpiece by the jaws, to therefore generate data representing a gripping procedure.

By using a mouthpiece that is used to clean or brush the user's teeth, data can be gathered over a long period of time (e.g. at least twice daily), rather than singly (e.g. at a specialist clinic or using a special device). This facilitates long-term analysis of properties of gripping by the upper and lower jaws, which can facilitate more accurate identification of dental occlusion disorders. In particular, tracking the measurements over time allow for increased accuracy in identifying persons at risk.

The one or more measurements of mechanical properties of the gripping may comprise: a force in one or more directions applied between a portion of the upper jaw and a portion of the lower jaw: and/or one or more components of a stress or pressure applied between a portion of the upper jaw and a portion of the lower jaw.

The force may, for instance, be a vertical force, being a (component of a) force applied in a direction normal to the plane in which the upper jaw lies. In some examples, the force may be a lateral force, being a (component of a) force applied a direction parallel to a plane in which the upper jaw lies. Of course, it will be appreciated that a direction of a force may lie between a vertical and lateral direction.

In some examples, the sensing arrangement comprises: a first sensor configured to sense a force or pressure applied between a first side of the upper jaw and a first side of the lower jaw: and a second sensor configured to sense a force or pressure applied between a second side of the upper jaw and a second side of the lower jaw, wherein the first side of the upper jaw is opposite to the second side of the upper jaw and the first side of the lower jaw is opposite to the second side of the lower jaw.

Differences in the pressure or force applied by different sides of the jaw. i.e. uneven pressure, can be indicative of a possible TMJ disorder or jaw misalignment.

The sensing arrangement may be configured to generate a difference measurement, being a difference between the force or pressure generated by the first sensor and the force or pressure generated by the second sensor.

The sensing arrangement may comprise a torque sensing arrangement configured to sense a torque applied to the lower jaw as the upper and lower jaws grip the mouthpiece.

The torque sensing arrangement may be configured to generate a measurement of rotation as the upper and lower jaws come together, and/or move apart, during a gripping of the mouthpiece.

A clamping or unclamping motion of the jaws will produce essentially no torque or rotation if the teeth are aligned (i.e. negligible torque will be produced). i.e. if there is correct jaw alignment, but will induce a torque or rotation if the teeth are not aligned. e.g. so that the upper and lower jaws are crossed. Monitoring a rotation of the mouthpiece using the torque sensor can therefore produce a measurement useful for assessing potential crossing of the jaws, to therefore predict or identify whether or not teeth are not aligned).

A pair of strain gauges, positioned at right angles (90°) to one another provides one suitable example of a torque sensing arrangement. Other torque sensing arrangements will be apparent to the skilled person.

In some examples, the torque sensing arrangement comprises: a first torque sensor configured to sense a torque applied to a first side of the upper jaw as the upper and lower jaws come together: and a second torque sensor configured to sense a torque applied to a second side of the lower jaw as the upper and lower jaws come together, wherein the first side of the lower jaw is opposite to the second side of the lower jaw.

A difference in the torque applied to the sides of the lower jaw can represent a misalignment between the jaws and/or more accurately identify a location of a misalignment between the jaws compared to a single torque sensor.

The sensing arrangement may comprise a motion sensor configured to generate a measurement of lateral motion or displacement or tilt of the mouthpiece as the upper and lower jaws come together, and/or move apart, during a gripping of the mouthpiece.

A side to side motion when the subject bites down (i.e. makes a clamping motion) or releases a bite is indicative of a misalignment or a difference in size of the upper and lower jaw. i.e. a jaw abnormality. This lateral side-to-side motion is measurable using a torque sensing arrangement. A lateral motion may be any motion that is parallel to a plane in which the upper jaw lies.

In one example, the sensing arrangement comprises two strain gauges positioned at right angles to each other, facilitating measurement of a torque and side-to-side motion. However in a simplified embodiment a single strain sensor may be appropriately positioned and configured to record the side to side motion alone.

Thus, in some examples, a torque sensing arrangement may be adapted to sense a side-to-side motion.

The one or more mouth contacting elements may comprise one or more sensing elements for the sensing arrangement, each sensing element being configured to sense a mechanical property of the gripping of the mount by the upper and lower jaws.

In particular, the one or more mouth contacting elements may be formed or made of a material that is able to sense the mechanical property. e.g. dynamic (static) pressure or force changes. In other words, at least part of the sensing arrangement may be integrated into the mouth contacting element(s).

In some examples, each sensing element comprises a conductive (e.g. elastomer) element configured to act as both a sensing element (e.g. force or muscle activity) and a bristle for cleaning the teeth and/or the gum of the subject.

The mouthpiece may further comprise an electromyography electrode arrangement configured to provide one or more signals that respond to electrical activity in one or more muscles of the jaw, for performing electromyography sensing.

One or more of the mouth contacting elements may be further configured to function as one or more electrode elements for the electromyography electrode arrangement. Thus, one or more of the mouth contacting elements may be at least partly conductive to thereby act as an electrode that generates a signal responsive to electrical activity in the muscles of the jaw. Suitable materials would be apparent to the skilled person, e.g. conductive silicone, conductive polymers and so on.

For instance, the one or more mouth contacting elements may comprise one or more brushing elements configured to clean/brush teeth and/or gums of the subject, wherein the one or more brushing elements are further configured to function as one or more electrode elements for the electromyography electrode arrangement.

In other words, one or more of the brushing elements may be at least partly conductive to thereby act as an electrode that generates a signal responsive to electrical activity in the muscles of the jaw. The brushing elements may, for instance, be formed of conductive silicone (or any other material) suitable for acting as an electrode and for brushing teeth/gums.

In some examples, the sensing arrangement is configured to comprise or function as one or more electrode elements for the electromyography electrode arrangement. e.g. the electrode elements may be integrated into the sensing arrangement.

In preferred examples, one or more sensors for the sensing arrangement and one or more electrodes for the electromyography electrode arrangement form part of the mouth contacting elements. e.g. ((partially) conductive) brushing elements may act as both sensors for the sensing arrangement and/or one or more electrodes for the electromyography arrangement.

In some examples, a first set of one or more mouth contacting elements are configured to act as a sensing element for the sensing arrangement and a second set of one or more mouth contacting elements are configured to act as an electrode element for the electromyography electrode arrangement. The first and second sets of mouth contacting elements may be exclusive, may partly overlap or may completely overlap.

One or more of the mouth contacting elements may thereby be configured to act as a sensing element for the sensing arrangement and an electrode element for the electromyography electrode arrangement.

The one or more mouth contacting elements may comprise one or more brushing elements for brushing or cleaning at least one gum or tooth of the subject.

The one or more mouth contacting elements may comprise: a mouthguard configured to cover and protect at least one part of the mouth of the subject, such as a gum and/or tooth: and/or a tooth alignment device configured to align or realign a position of a tooth of the subject. The one or more mouth contacting elements may comprise a bite guard.

It will be appreciated that in some examples, the mount and the mouth contacting element may be the same element. e.g. where the mount provides a mouthguard for covering and protecting one or more parts of the mouth of the subject.

There is also proposed a mouthpiece system comprising: the mouthpiece previously described: and a processing arrangement configured to: receive, from the sensing arrangement of the mouthpiece, the one or more measurements of the mechanical properties of the gripping: and process the received one or more measurements to generate an indicator that indicates whether or not there are one or more abnormalities in the upper and/or lower jaws of the subject.

The processing arrangement may receive the one or more measurements at an input interface of the processing arrangement.

The mouthpiece system may further comprise a memory configured to iteratively store the one or more measurements obtained by the sensing arrangement, to thereby form stored measurements: wherein the processing arrangement is configured to process the received one or more measurements and the stored one or more measurements to generate the indicator.

The processing arrangement may be configured to control a user interface to provide a visual representation or user-perceptible output of the one or more measurements and/or any generated indicators (if generated). Thus, the processing arrangement may be configured to output (e.g. at an output interface) an interface control signal for controlling the operation of the user interface.

In some examples, the processing arrangement may be configured to control a user interface to instruct the subject to perform a guided biting maneuver, e.g. in the form of a textual or visual output. This embodiment enables well-controlled and predictable (un-)gripping of teeth with respect to the mount as part of a user workflow, for increased consistency in obtaining measurements.

The mouthpiece system may further comprise the user interface.

These and other aspects of the invention will be apparent from and elucidated with reference to the embodiment(s) described hereinafter.

BRIEF DESCRIPTION OF THE DRAWINGS

For a better understanding of the invention, and to show more clearly how it may be carried into effect, reference will now be made, by way of example only, to the accompanying drawings, in which:

FIG. 1 illustrates a mouthpiece according to an embodiment:

FIG. 2 illustrates a sensor for use in a sensing arrangement:

FIG. 3 is a cross-section of a mouthpiece according to an embodiment:

FIG. 4 illustrates a torque sensing arrangement for use in an embodiment:

DETAILED DESCRIPTION OF THE EMBODIMENTS

Figure 5:
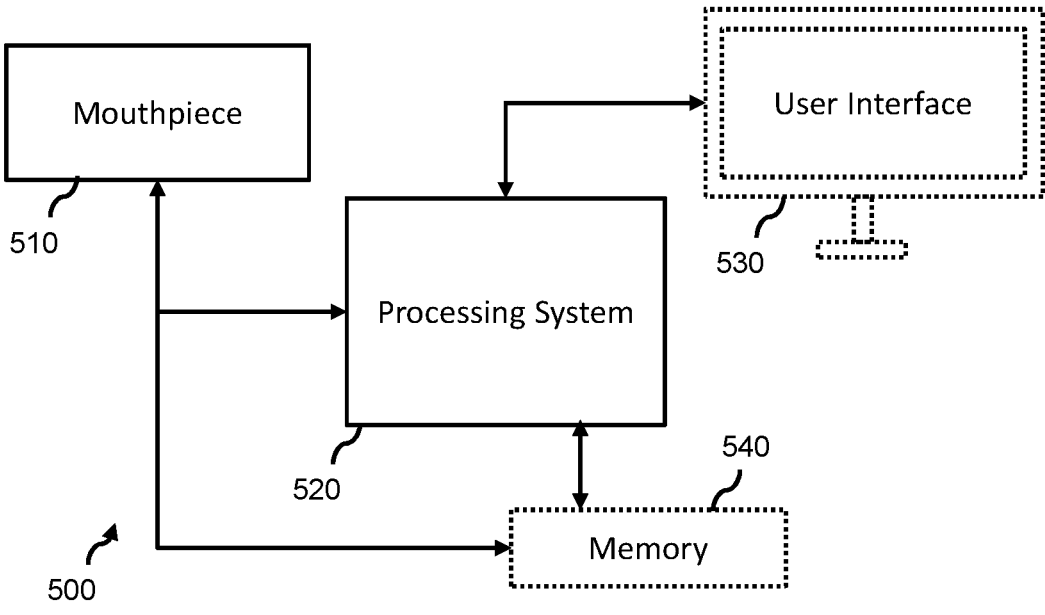
FIG. 5 illustrates a mouthpiece system according to an embodiment.

The invention will be described with reference to the Figures.

It should be understood that the detailed description and specific examples, while indicating exemplary embodiments of the apparatus, systems and methods, are intended for purposes of illustration only and are not intended to limit the scope of the invention. These and other features, aspects, and advantages of the apparatus, systems and methods of the present invention will become better understood from the following description, appended claims, and accompanying drawings. It should be understood that the Figures are merely schematic and are not drawn to scale. It should also be understood that the same reference numerals are used throughout the Figures to indicate the same or similar parts.

The invention provides an approach for obtaining measurements of mechanical properties of a gripping performed by masticatory apparatus. A mouthpiece provides a sensing arrangement (for obtaining the measurement) and one or more mouth contacting elements for protecting, cleaning or treating teeth/gums. In this way, measurements indicative of potential abnormalities or physiological dysfunction in the masticatory apparatus can be obtained using a mouthpiece that has a secondary or further function of protecting, aligning, cleaning and/or treating elements of the mouth.

It will be appreciated that the "secondary function" may in fact be the primary intended use function for the mouthpiece. e.g. the advertised function of the mouthpiece, with the features of the present disclosure forming additional useful functionality for the mouthpiece. The term "secondary function" has been used to distinguish the protecting, cleaning and/or treatment functionality from the mechanical property sampling functionality described in this disclosure.

Embodiments of the invention advantageously recognize that the integration of such sensing capability into a mouthpiece having a secondary (oral care or health) function facilitates improved ease and regularity of obtaining measurements. This is based on a realization that the onset of abnormalities or physiological dysfunction in the masticatory apparatus can be detected by monitoring changes in mechanical properties of a gripping (e.g. of a bite) over a period of time. By using a mouthpiece with a secondary function, a likelihood that repeated measurements over a period of time will take place can increase (by relying upon a subject's regular use of the mouthpiece).

The proposed concepts can be employed in any mouthpiece that can be held between the upper and lower jaws, such as cleaning (e.g. brushing) apparatus, orthodontic retainers/aligners, mouth guards, bite guards, mandibular advancement devices and so on.

In the context of the present application, the masticatory apparatus refers to the upper and lower jaws (inclusive of any teeth or dental implants) of a subject, together with other anatomical features that contribute to the movement of the upper and lower jaws (e.g. jaw muscles and/or the temporomandibular joint).

FIG. 1 illustrates a mouthpiece 100 according to an embodiment of the invention. The mouthpiece is designed or configured to be held in the mouth of a subject.

The mouthpiece 100 comprises a mount 110. The mount is configured to be gripped or grippable between upper and lower jaws of the subject. Thus, the mount may be appropriately shaped and/or sized to fit within a mouth of the subject so that the subject is able to "bite down" on the mouthpiece, so as to grip the mount 110 between their jaws. For instance, the mount may have a (tooth-) arch like shape, a chevron shape, a semi-circular shape and so on. The mount may, for example, be custom-made from oral scans of the subject, or of a pre-determined shape/size that best fits to the subject's dentition (i.e. the best fitting mount taken from a set of predetermined or fixed (and different) mount sizes).

In the illustrated example, the mount is in the shape of a half-annulus (i.e. a sector of an annulus where the segmenting line passes through a diameter of the annulus).

The gripping does not need not be caused by direct contact between the jaws and the mount. e.g. gripping may take place via one or more intermediate elements (such as those later described).

In the context of the present application, a gripping occurs when a mouthpiece (i.e. the mount) is held between the jaws of the subject. This does not need to be a tight or clamped grip, and could be a loose grip (e.g. where the mouthpiece is loosely held). Any movement during a gripping (e.g. a clamping or declamping, clenching or unclenching, biting down or releasing a bite) may be random or well-controlled through instruction given to the user to perform a guided biting maneuver.

The mount 110 may further comprise a stopper 115, which is configured to contact the front of the teeth or lips of the subject, to prevent or restrict the movement of the mouthpiece towards the back of the throat. This can help prevent unintentional gagging on the mouthpiece and/or act as a guide for positioning the mouthpiece within the mouth of the subject.

The mouthpiece 100 further comprises one or more mouth contacting elements 120. A mouth contacting elements is configured to perform one or more protection, cleaning and/or (dental) treatment tasks. In particular, a mouth contacting element is configured to contact one or more parts of the mouth and perform a protection, cleaning, alignment and/or (dental) treatment task to the contacted parts of the mouth. A part of the mouth may include a tooth, a gum, a tongue and/or a dental implant. A (dental) treatment may include any suitable treatment task such as an alignment task (e.g. using a retainer or brace(s)) and/or a tooth whitening task. Thus, dental treatment may include cosmetic and non-cosmetic procedures.

In the illustrated example, each mouth contacting element 120 is/comprises a brushing element for brushing (i.e. cleaning) one or more teeth and/or gums of the subject. However, other types of mouth contacting elements could be used in addition or instead of the brushing element(s), such as a mouthguard, a bite guard, a mandibular advancement device (MAD), a (tooth) alignment device, a (orthodontic) retainer and so on.

The mouthpiece 100 further comprises a sensing arrangement 130. The sensing arrangement is positioned in or on the mount 110. During gripping of the mount by the upper and lower jaws (i.e. when the mouthpiece is being held between the jaws), the sensing arrangement senses one or measurements of mechanical properties of the gripping by the upper and lower jaws. Put another way, the sensing arrangement may sense one or more measurements of mechanical properties exerted on the mouthpiece responsive to, or as a result of, a gripping by the upper and lower jaws, which may include measurements of changes in the mechanical properties due to changes in the gripping. e.g. during a bite down or release.

Suitable examples of mechanical properties include pressure, stress, force, torque, strain, displacement, motion, orientation/tilt (e.g. as a result of abnormalities of the upper/lower jaw) and so on. The skilled person would be readily capable of developing or using sensing arrangements for detecting such mechanical properties following the teachings of this disclosure.

The measurements of the mechanical properties of (the result of) the gripping are measurements that are responsive to one or more abnormalities or physiological dysfunction in the masticatory apparatus of the subject. Thus, the measurements of mechanical properties may be those that have a conventional or desired value for a subject or those that should not (significantly) change over repeated use of the jaws and/or over time.

In particular, the sensing arrangement may be configured to sense measurements of one or more mechanical properties of the gripping during a clamping motion of the subject (where the lower jaw applies pressure, or increase pressure applied, to the upper jaw) and a unclamping/declamping motion of the subject (where the lower jaw stops applying, or reduces pressure applied, to the upper jaw). It has been recognized that measurements during a clamping/declamping process are particularly responsive to and indicative of abnormalities or physiological dysfunction in the masticatory apparatus such as the TMJ. This is because such TMJ abnormalities or physiological dysfunction(s) can cause a change in the motion of the lower jaw during a clamping operation.

The present invention recognizes that sensing arrangements for obtaining such measurements (suitable for identifying masticatory apparatus disorders or degradation symptoms) can be integrated into a mouthpiece having a secondary function. e.g. a protective, cleaning or treatment function. This means that long-term data about the measurements of the subject can be obtained, e.g. as the mouthpiece may be regularly used for its secondary function over time, which means that such measurements can be obtained without requiring a dedicated measurement session.

The sensing arrangement may be capable of obtaining a measurement of a mechanical property of the gripping at multiple positions of the mouthpiece (e.g. for different parts of the mouth). In this way, a mapping of measurements of the gripping performed by the upper and lower jaws can be carried out. A measurement map is helpful in identifying areas of unusual anatomy or gripping between the upper and lower jaws, and therefore potential abnormalities or physiological dysfunction in the masticatory apparatus.

As one example only, a measurement may be a measurement of a force applied between a particular part of the upper jaw and a corresponding part of the lower jaw, where multiple measurements/samples are obtained (e.g. at a same time) for different parts of the upper and lower jaws.

Preferably, the one or more measurements of mechanical properties of the gripping include a component of a force, stress or pressure applied between a portion of the upper jaw and a portion of the lower jaw. Preferably, multiple measurements are made/sampled. e.g. for different portions of the upper/lower jaw and/or at different points in time.

The sensing arrangement 130 may be at least partly integrated into the mouth contacting element 120. For instance, the brushing element(s) may comprise material suitable for acting as (part of) a sensing arrangement. By way of example, a brushing element may comprise conductive silicone pillars/elements that can be used as a force/ pressure measurement sensor, as well as bristles/tufts (mounted on the silicone pillars) for cleaning teeth and/or gums.

However. (complete) integration of the sensing arrangement into the mouth contacting element is not essential, and the sensing arrangement may comprise one or more elements positioned elsewhere in/on the mount. For example, higher resolution force/pressure measurements may be obtained using thin, flexible pressure sensitive films positioned in/on the mount of the mouthpiece (e.g. by over-molding).

The illustrated sensing arrangement 130 comprises a first sensor 131 configured to sense (a component of) a force, stress or pressure applied between a first side of the upper jaw and a first side of the lower jaw (e.g. a force/stress/pressure applied to a first side 101 of the mouthpiece). The sensing arrangement 130 also comprises a second sensor 131 configured to sense a (component of a) force, stress or pressure applied between a second side of the upper jaw and a second side of the lower jaw (e.g. a force, stress of pressure applied to a second side 102 of the mouthpiece 100). The first side of the upper jaw is opposite to the second side of the upper jaw and the second first side of the lower jaw is opposite to the second side of the lower jaw.

Although only two sensors are illustrated, the sensing arrangement may comprise any number of sensors. e.g. only a single sensor (element), a plurality of sensors, four or more sensors, six or more sensor and so on. It is not essential that each sensor measure/sense the same type of physical component of the gripping performed by the upper and lower jaws.

In the illustrated example, the first sensor and the second sensor are both integrated into the mouth contacting elements. In particular, both sensors are formed from force-sensitive or pressure-sensitive material (e.g. particle filled conductive silicone or conductive polymer(s)) of the brushing elements of the mouth contacting elements. An example of a sensor formed of suitable material is described by the U.S. patent Ser. No. 10/736,528 B2, which could be adapted for use with embodiments of the present disclosure. Thus, one or more brushing elements may produce a signal that responds to differing amounts of force, pressure or stress being applied thereto. A brushing element may therefore be a (partially) conductive bristle.

Due to its conductive nature, the brushing elements can be also used as passive electrode to measure electrophysiological signals in the mouth (e.g. electromyography: EMG) as explained later below.

FIG. 2 illustrates one example of a suitable sensor 200 that can act as a mouth contacting element and part of a sensing arrangement.

The sensor 200 is in the form of a structured pin electrode with an electrode body 202 and an electrical coupling or snap 210. In some embodiments, a structured pin electrode 200 may be used. In some embodiments, structured pin electrode 200 may include a multi-pin design (e.g., comprising one or more pins 250) that enables electrode 200 to establish a good galvanic contact with the subject.

The (e.g. each) pin 250 is formed of a particle filled conductive silicon material (or other suitable material such as conductive polymer(s)) that is force-sensitive and/or pressure-sensitive, and is able to act as a brush for the mouth of the subject. In other words, the pin 250 may act as a bristle or brushing element for the mouth. Thus, the pin 250 may effectively be a conductive bristle.

In some embodiments, electrode 200 may have a diameter of 25 millimeters. In some embodiments, pin 250 of elec-trode 200 may have a height of 5 millimeters. In some embodiments, pin 250 of electrode 200 may have a diameter of 2 millimeters.

Turning back to FIG. 1, the skilled person would appreciate that the first sensor and second sensor could be formed elsewhere, e.g. in force/pressure/stress-sensitive film positioned on top of, or integrate into the mount 110, e.g. by over-molding.

The illustrated sensing arrangement 130 is further configured to generate a difference measurement (which could be alternatively labelled a differential measurement). The difference measurement is a difference between the force, pressure or stress detected by the first sensor and the force, pressure or stress detected by the second sensor. The sensing arrangement may comprise a difference measurement sensor 135 for performing this measurement.

The difference measurement effectively provides a measurement of force/pressure difference between contralateral sites in the mouth. It has been identified that a difference in the force/pressure/stress being applied between contralateral sites is responsive to abnormalities or physiological dysfunction in the masticatory apparatus, such as the presence of a TMJ disorder. Such a measurement therefore provides useful information In some other examples, a force or pressure obtained at a first sensor 131 and the second sensor 132 is determined with respect to a reference measurement, e.g. a force or pressure measured at a third, reference sensor (not shown).

The mouthpiece 100 may further comprise an electro-myography (EMG) electrode arrangement 140 configured to generate one or more signals that respond to electrical activity in (one or more muscles of) the jaw(s).

In one embodiment, the EMG measurement is facilitated or performed by one or more of the mouth contacting elements, e.g. a brushing element and/or the sensing arrangement. For instance, EMG measurement may be facilitated by the conductive nature of the previously described brushing elements and/or sensing arrangements and could be performed using a sensing arrangement/element 131 (that is also able to act as a (lateral) brushing element integrated in the mount 110).

By way of example, with reference to FIG. 2, the conductive support plate 200 and/or conductive bristles 250 of the illustrated sensor 200 could be used to measure EMG.

The EMG electrode arrangement 140 may comprise one or more electrodes positioned on the mount 110. These electrodes may be dedicated electrodes (i.e. electrodes not used for any other purpose) or may be (at least partially) integrated into the mouth contacting element(s) 120 and/or sensing arrangement 130. For instance, a mouth contacting element may comprise one or more brushing elements, of which at least one may be at least partially conductive so as to act as an electrode for the EMD electrode arrangement.

In the illustrated example, the EMG system comprises two electrodes configured to perform EMG measurements. However, any number of electrodes could be used. e.g. a single electrode, two or more electrodes, such as four electrodes, eight electrodes and so on.

Preferably, the one or more electrodes 140 are positioned at a distal end of the mouthpiece (i.e. at the end of the mouthpiece received towards the back of the throat) and/or face the buccal (cheek) side of the jaw. This aids in the acquisition of EMG measurements from the masseter muscle, which is herein identified as being particularly indicative of abnormalities or physiological dysfunction in the masticatory apparatus. In particular, such EMG measurements are responsive to the presence of a TMJ disorder.

In some examples, the one or more electrodes are mounted on a side of the mount. e.g. a side on the outer perimeter of the mount. This increases the likelihood that the one or more electrodes will make contact with a muscle for sensing electrical activity thereof.

In particular preferable examples, the one or more electrodes are positioned so that when the mouthpiece is received by the mouth of the subject (so that the mount is gripped between the upper and lower jaws), then the electrodes make contact with a cheek of the subject.

It has previously been mentioned how the EMG electrode may be at least partially integrated into the mouth contacting element(s). In particular, a mouth contacting element may comprise or be formed of a material sensitive or responsive to electrical signals (i.e. material suitable for forming an electrode).

FIG. 3 is a side-view illustrating a cross-section of a mouthpiece 300 according to another embodiment.

The mouthpiece 300 comprises a mount 310 and one or more mouth contacting elements 320 supported by the mount 310. Here, the mouth contacting elements again comprise one or more brushing elements, although other forms of mouth contacting element for protecting, cleaning or treating the teeth are envisaged.

The mouthpiece comprises a sensing arrangement 330, which is integrated into the mount. i.e. between a first portion 311 and a second portion 312 of the mount. In the illustrated example, a first set of mouth contacting elements is coupled to an upper surface 311A of the mount 310 and a second set of mouth contacting element is coupled to a lower surface 312A of the mount 310. One or more of these sets may be omitted.

In alternative examples, the mount is formed of one continuous portion (e.g. the second portion 312 is omitted), the sensing arrangement 330 is mounted on this portion and the second set of one or more mouth contacting elements are directed mounted on the sensing arrangement.

Here, the sensing arrangement 330 comprises a torque sensing arrangement configured to detect a torque applied to/by the lower jaw to the torque sensing arrangement as the upper and lower jaws come together (or move apart). In particular, the torque sensing arrangement may be positioned to detect any lateral torque applied to the torque sensing arrangement. A lateral torque is a torque applied about an axis that lies parallel to a plane in which the upper teeth lie, and which spans from a rear of the mouth to a front of the mouth. The torque sensing arrangement may thus be configured and positioned so that, if the teeth are aligned when the upper and lower jaws come together (or move apart), then no torque is detected and if teeth are not aligned when the upper and lower jaws come together (or move apart), then torque is detected.

Thus, a torque present during a clamping or declamping process may be detected. In particular, a torque sensing arrangement may detect a torque applied to the mouthpiece about an axis that is parallel to a plane in which the upper jaw lies, to thereby detect whether a crossing or planar misalignment of the jaws has occurred (i.e. so that the teeth are not aligned) or a dysfunction in the TMJ exists.

In some examples, a torque measurement may be taken during a clamping process (i.e. as the jaws come together) and during a declamping process (i.e. as the jaws move apart). This feature enables the quality of the torque measurements to be confirmed, as in the ideal case the signals when biting and releasing should be equal in amplitude and opposite in sign.

FIG. 4 illustrates an example of a suitable torque sensing arrangement 400 for use in the sensing arrangement of FIG. 3. The torque sensing arrangement is formed of a first strain gauge 410 and a second strain gauge 420 positioned orthogonally to one another. This facilitates the sampling and/or obtaining of a torque measurement.

The foregoing examples provide various approaches and system for obtaining measurements of physical/mechanical properties of the gripping performing by (upper and lower jaws of) the masticatory apparatus, which can be used to assess a condition of the masticatory apparatus. e.g. automatically or by a clinician.

However, the described measurements of physical/mechanical properties are not considered exhaustive. Rather, a sensing arrangement may be configured to obtain/sample measurements of any suitable property that indicates or is responsive to an onset, worsening or change in abnormalities or physiological dysfunction in the masticatory apparatus of the subject.

By way of further example, a sensing arrangement of a mouthpiece may comprise a motion sensor configured to sense a side-to-side motion (e.g. sliding) of the lower jaw and/or the mouthpiece during a clamping or declamping process of the jaws. A side-to-side motion (i.e. a lateral motion) is an example of a measurement indicative of either a misalignment or a difference in size of the upper and lower jaw.

In the context of the present application, a side-to-side motion is a motion in a plane parallel to a plane in which the upper jaw lies.

This sensing arrangement may, for instance, comprise another torque sensing arrangement. e.g. comprising two strain gauges positioned at right angles (i.e. orthogonally) to each other. However in a less expensive embodiment a single strain sensor positioned to sense or record the side-to-side motion would be sufficient.

As yet another example, a sensing arrangement of a mouthpiece may be configured to calculate, sense or measure a distance (or relative displacement/offset) between different parts of the upper and lower jaw during a clamping or declamping motion. If subject's bite is uneven (indicative of potential abnormalities or physiological dysfunction in the masticatory apparatus), then a distance between different parts of the upper and lower jaw will be different.

As yet another example, a sensing arrangement of a mouthpiece may be configured to calculate, sense or measure an orientation (e.g. tilting) of the upper and/or lower jaws (e.g. with respect to one another) during a gripping of the mouthpiece. e.g. during a clamping or declamping motion of the mouthpiece. Typically, the upper and lower jaws should have a same or similar orientation when gripping a mouthpiece (i.e. they should be parallel to one another). A deviation from a same/similar orientation could be indicative of potential abnormalities or physiological dysfunction in the masticatory apparatus.

As yet another example, a sensing arrangement of a mouthpiece may be configured to calculate, sense or measure an angle between the upper and/or lower jaws (e.g. with respect to one another) during a gripping of the mouthpiece. e.g. during a clamping or declamping motion of the mouthpiece. The sensing arrangement may therefore comprise a (digital) goniometer, a (2D) gimbal angulation sensor and/or an accelerometer. Other suitable types of sensors will be apparent to the skilled person. As previously explained, the jaws should be mostly parallel when gripping a mouthpiece, such that presence or size of an angle between the jaws is indicative of potential abnormalities or physiological dysfunction in the masticatory apparatus.

In another example, the sensing arrangement may be configured to calculate, sense or measure could be a 3D force and momentum measurement using an integrated piezoelectricity based force dynamometer which allows to capture both static and dynamic biting forces or torque changes.

The skilled person will appreciate that a sensing arrangement may be configured to detect a combination of any previously described measurements and/or mechanical properties of the gripping of the mouthpiece by the upper and lower jaws. The skilled person would be capable of modifying the sensing arrangement to include, where appropriate, one or more of the sensors (e.g. the force sensing arrangement, the torque sensing arrangement and so on) previously described.

Any herein described embodiment may also comprise the electromyography (EMG) electrode arrangement configured to generate one or more signals that respond to electrical activity in (one or more muscles of) the jaw(s).

Whilst only a single mouthpiece has been described in the foregoing examples, it will be apparent that a subject may grip a plurality of mouthpieces in their mouth (e.g. one mounted on an upper jaw and one mounted on a lower jaw). One or more of these mouthpieces may be a mouthpiece as previously described.

FIG. 5 is a block diagram illustrating a mouthpiece system 500 according to an embodiment. The mouthpiece system comprises a mouthpiece 510 (such as any previously described mouthpiece) and a processing arrangement 520. The mouthpiece 510 may be one of a plurality of mouthpieces for a subject.

The processing arrangement is configured to receive, from the sensing arrangement of the mouthpiece, the one or more measurements of the mechanical properties of the gripping. In some examples, the processing arrangement is configured to monitor the measurements provided by the sensing arrangement and (periodically) sample the measurements.

The processing arrangement may communicate with the sensing arrangement via one or more wires and/or via a wireless communication mechanism. Suitable wireless communication mechanisms will be readily apparent to the skilled person. Suitable wireless communication protocols and may include an infrared link. ZigBee®, Bluetooth®, a wireless local area network protocol such as in accordance with the IEEE R: 802.11 standards, a 2G, 3G or 4G telecommunication protocol, and so on. Other formats will be readily apparent to the person skilled in the art.

Where the mouthpiece 510 is one of a plurality of mouthpieces, it will be appreciated that each mouthpiece may provide one or more measurements of the gripping of the mouthpieces.

The processing arrangement 520 may be configured to process the received one or more measurements to generate an indicator that indicates whether or not there are any abnormalities or physiological dysfunction in the masticatory apparatus.

The indicator may be one or more of: a binary indicator that predicts whether or not the there are any abnormalities or physiological dysfunction in the masticatory apparatus: a categorical indicator that provides (if relevant) a predicted type or classification of abnormality or physiological dysfunction identified in the masticatory apparatus: and/or a numeric indicator that provides a likelihood (e.g. on a scale of 0) to 1, 0 to 100, 0 to 10, 1 to 10 or 1 to 100) that there are any abnormalities or physiological dysfunction in the masticatory apparatus. More than one indicator may be generated in some embodiments. e.g. a plurality of different binary or numeric indicators for different types of classifications of abnormality or physiological dysfunction.

Processing may comprise, for instance, comparing any received measurements to one or more (predetermined) thresholds to determine or predict whether any such abnormalities or physiological dysfunction exists and/or how severe the abnormality is.

Purely by way of example, consider a scenario in which a measurement obtained by the processing arrangement is a difference measurement that indicates a difference between the force applied between a first side of the upper and lower jaws and a force applied between a second, different side of the upper and lower jaws. In this scenario, an abnormality or physiological dysfunction may be predicted to exist if the difference measurement exceeds some predefined value (as an uneven force is indicative of an abnormality or physiological dysfunction).

Another approach could be to process received measurements using a machine-learning method to generate an indicator, where the machine-learning indicator has been trained to detect abnormalities or physiological dysfunction in the masticatory apparatus based on a set of one or more measurements received as input. Comparison with federated data can also allow for a disease classification.

Yet another approach could be to compare received measurements to historic measurements. An increase in a particular measurement could be indicative of an onset of an abnormality and/or physiological dysfunction. Thus, processing may comprise determining if a change in a particular measurement (e.g. over time) exceeds some threshold. Here, a change may be a difference between a previous measurement and a most recently acquired measurement and/or a ratio between such a difference and a time difference between a time at which the previous measurement was acquired and a time at which a most recently acquired measurement was acquired.

More generally, longitudinal measurements (i.e. measurements over time) allow for the tracking of disease progression or response to therapy and/or natural healing.

Where appropriate, the processing arrangement 520 may also receive any generated signals, by the optional electromyography (EMG) electrode arrangement of the mouthpiece, that respond to electrical activity in (one or more muscles of) the jaw(s). Processing the received one or more measurements to generate the indicator may comprise processing the received one or more measurements and the received signals to determine whether there are any abnormalities or physiological dysfunction in the masticatory apparatus.

It will be appreciated that the processing arrangement 520 may be configured to receive, as input, one or more other parameters or measurements when processing the received measurements to generate the indicator that indicates whether or not there are any abnormalities or physiological dysfunction in the masticatory apparatus. These one or more other parameters or measurements may include, for instance, subject information, such as an age, gender, weight, medical history, signs, symptoms, diagnoses and so on.

In some examples, the mouthpiece system may further comprise a user interface 530. The processing arrangement 520 may be configured to control the user interface to provide a visual representation or user-perceptible output of the one or more measurements and/or any generated indicators (if generated).

In some examples, the mouthpiece arrangement further comprises a memory 540, configured to iteratively store the one or more measurements obtained by the sensing arrangement. In this way, measurements obtained over a period of time (e.g. in different sessions of using the mouthpiece by the user or when the subjects uses a new mouthpiece after some time) can be stored.

Various forms of memory are envisaged, for instance, any one or combination of volatile memory elements (e.g., random access memory (RAM), such as dynamic random access memory (DRAM), static random access memory (SRAM), etc.) and non-volatile memory elements (e.g., ROM, erasable programmable read only memory (EPROM), electronically erasable programmable read only memory (EEPROM), programmable read only memory (PROM), tape, compact disc read only memory (CD-ROM), disk, diskette, cartridge, cassette or the like, etc.). Moreover, the memory may incorporate electronic, magnetic, optical, and/or other types of storage media. Note that the memory 540 can have a distributed architecture, where various components are situated remote from one another, but can be accessed by the processing system 520.

The processing arrangement 520 may be configured to process the stored measurement(s) and the obtained measurements to generate the indicator. In this way, the indicator may be generated on the basis of historic and current measurements of mechanical properties of the gripping performed between upper and lower jaws.

This embodiment recognizes that changes in mechanical properties can indicate the onset of abnormalities or physiological dysfunction in the masticatory apparatus, such as the presence of a TMJ disorder.

Thus, the processing performed by the processing arrangement 520 may comprise comparing one or more current measurements (i.e. most recently acquired) to historic or stored measurement(s). A deviation of more than a predetermined amount (e.g. percentage or amount) may be indicative of a potential abnormality or physiological dysfunction in the masticatory apparatus.

Alternatively, the processing performed by the processing arrangement 520 may comprise processing a time-series or sequence of obtained measurements (including the stored measurements and the most recently obtained measurement(s)) to generate the indicator. This embodiment recognizes that a change of measurements over time is indicative of the onset of a potential abnormality or physiological dysfunction in the masticatory apparatus.

Figure 6:
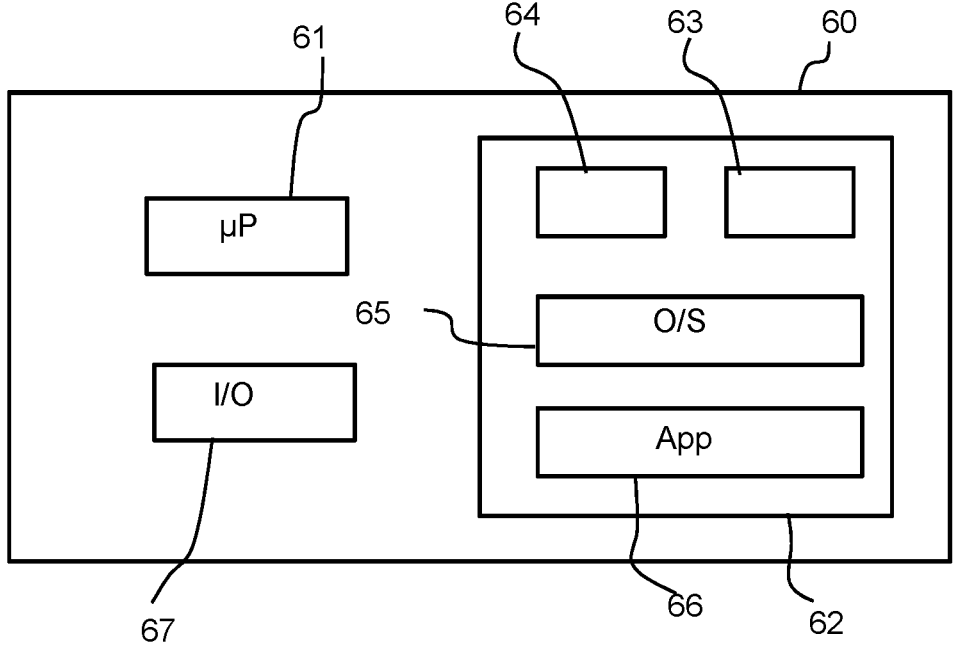
FIG. 6 illustrates a processing system for use in an embodiment.

By way of further example. FIG. 6 illustrates an example of a processing system 60 for use in an embodiment. Various operations discussed above may utilize the capabilities of the processing system 60. For example, one or more parts of a system for obtaining and processing measurements from a herein described mouthpiece may be incorporated in any element, module, application, and/or component discussed hereafter. In this regard, it is to be understood that system functional blocks can run on a single processing system or may be distributed over several computers and locations (e.g. connected via internet).

The processing system 60 includes, but is not limited to, PCs, workstations, laptops. PDAs, palm devices, servers, storages, and the like. Generally, in terms of hardware architecture, the processing system 60 may include one or more processors 61, memory 62, and one or more I/O devices 67 that are communicatively coupled via a local interface (not shown). The local interface can be, for example but not limited to, one or more buses or other wired or wireless connections, as is known in the art. The local interface may have additional elements, such as controllers, buffers (caches), drivers, repeaters, and receivers, to enable communications. Further, the local interface may include address, control, and/or data connections to enable appropriate communications among the aforementioned components.

In some examples, the memory is external to the processing system, e.g. as perhaps best illustrated in FIG. 5.

Turning back to FIG. 6, the processor 61 is a hardware device for executing software that can be stored in the memory 62. The processor 61 can be virtually any custom made or commercially available processor, a central processing unit (CPU), a digital signal processor (DSP), or an auxiliary processor among several processors associated with the processing system 60, and the processor 61 may be a semiconductor based microprocessor (in the form of a microchip) or a microprocessor.

The memory 62 can include any one or combination of volatile memory elements, such as dynamic random access memory and non-volatile memory elements. Suitable examples of such elements have been previously provided. Moreover, the memory 62 may incorporate electronic, magnetic, optical, and/or other types of storage media. Note that the memory 62 can have a distributed architecture, where various components are situated remote from one another, but can be accessed by the processor 61.

The software in the memory 62 may include one or more separate programs, each of which comprises an ordered listing of executable instructions for implementing logical functions. The software in the memory 62 includes a suitable operating system (O/S) 65, compiler 64, source code 63, and one or more applications 66 in accordance with exemplary embodiments. As illustrated, the application 66 comprises numerous functional components for implementing the features and operations of the exemplary embodiments. The application 66 of the processing system 60 may represent various applications, computational units, logic, functional units, processes, operations, virtual entities, and/or modules in accordance with exemplary embodiments, but the application 66 is not meant to be a limitation.

The operating system 65 controls the execution of other processing system programs, and provides scheduling, input-output control, file and data management, memory management, and communication control and related services. It is contemplated by the inventors that the application 66 for implementing exemplary embodiments may be applicable on all commercially available operating systems.

Application 66 may be a source program, executable program (object code), script, or any other entity comprising a set of instructions to be performed. When a source program, then the program is usually translated via a compiler (such as the compiler 64), assembler, interpreter, or the like, which may or may not be included within the memory 62, so as to operate properly in connection with the O/S 65. Furthermore, the application 66 can be written as an object oriented programming language, which has classes of data and methods, or a procedure programming language, which has routines, subroutines, and/or functions, for example but not limited to, C, C++, C #, Pascal, BASIC, API calls, HTML, XHTML, XML, ASP scripts, JavaScript, FORTRAN, COBOL, Perl, Java, ADA, .NET, and the like.

The I/O devices 67 may include input devices such as, for example but not limited to, a mouse, keyboard, scanner, microphone, camera, etc. Furthermore, the I/O devices 67 may also include output devices, for example but not limited to a printer, display, etc. Finally, the I/O devices 67 may further include devices that communicate both inputs and outputs, for instance but not limited to, a NIC or modulator/demodulator (for accessing remote devices, other files, devices, systems, or a network), a radio frequency (RF) or other transceiver, a telephonic interface, a bridge, a router, etc. The I/O devices 67 also include components for communicating over various networks, such as the Internet or intranet.

If the processing system 60 is a PC, workstation, intelligent device or the like, the software in the memory 62 may further include a basic input output system (BIOS) (omitted for simplicity). The BIOS is a set of essential software routines that initialize and test hardware at startup, start the O/S 65, and support the transfer of data among the hardware devices. The BIOS is stored in some type of read-only-memory, such as ROM, PROM. EPROM, EEPROM or the like, so that the BIOS can be executed when the processing system 60 is activated.

When the processing system 60 is in operation, the processor 61 is configured to execute software stored within the memory 62, to communicate data to and from the memory 62, and to generally control operations of the processing system 60 pursuant to the software. The application 66 and the O/S 65 are read, in whole or in part, by the processor 61, perhaps buffered within the processor 61, and then executed.

When the application 66 is implemented in software it should be noted that the application 66 can be stored on virtually any processing system readable medium for use by or in connection with any processing system related system or method. In the context of this document, a processing system readable medium may be an electronic, magnetic, optical, or other physical device or means that can contain or store a processing system program for use by or in connection with a processing system related system or method.

The application 66 can be embodied in any computer-readable medium for use by or in connection with an instruction execution system, apparatus, or device, such as a computer-based system, processor-containing system, or other system that can fetch the instructions from the instruction execution system, apparatus, or device and execute the instructions. In the context of this document, a "computer-readable medium" can be any means that can store, communicate, propagate, or transport the program for use by or in connection with the instruction execution system, apparatus, or device. The processing system readable medium can be, for example but not limited to, an electronic, magnetic, optical, electromagnetic, infrared, or semiconductor system, apparatus, device, or propagation medium.

Variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality.

A single processor or other unit may fulfill the functions of several items recited in the claims.

The mere fact that certain measures are recited in mutually different dependent claims does not indicate that a combination of these measures cannot be used to advantage. If the term "adapted to" is used in the claims or description, it is noted the term "adapted to" is intended to be equivalent to the term "configured to". Any reference signs in the claims should not be construed as limiting the scope.

The invention claimed is:

1. A mouthpiece comprising:
   a mount configured to be gripped between upper and lower jaws of a subject;
   one or more mouth contacting elements, each being configured to contact one or more parts of the mouth of the subject and treat and/or clean the contacted one or more parts of the mouth when the mount is gripped between the upper and lower jaws; and
   a sensing arrangement positioned in or on the mount, wherein the sensing arrangement is configured to sense, during gripping of the mount by the upper and lower jaws of the subject, one or more measurements of mechanical properties of the gripping by the upper and lower jaws,
   wherein the one or more measurements of the mechanical properties are responsive to one or more abnormalities or physiological dysfunction in masticatory apparatus of the subject,
   wherein the sensing arrangement comprises:
      a first sensor configured to sense a force or pressure applied between a first side of the upper jaw and a first side of the lower jaw; and
      a second sensor configured to sense a force or pressure applied between a second side of the upper jaw and a second side of the lower jaw, wherein the first side of the upper jaw is opposite to the second side of the upper jaw and the first side of the lower jaw is opposite to the second side of the lower jaw,
   wherein the sensing arrangement is configured to generate a difference measurement, being a difference between the force or pressure generated by the first sensor and the force or pressure generated by the second sensor,
   wherein the sensing arrangement comprises a torque sensing arrangement configured to sense a torque applied to the lower jaw as the upper and lower jaws grip the mouthpiece.

2. The mouthpiece of claim 1, wherein the one or more measurements of mechanical properties of the gripping comprises one or more of:
   a force in one or more directions applied between a portion of the upper jaw and a portion of the lower jaw; and/or
   one or more components of a stress or pressure applied between a portion of the upper jaw and a portion of the lower jaw.

3. The mouthpiece of claim 1, wherein the torque sensing arrangement is configured to generate a measurement of rotation as the upper and lower jaws come together, and/or move apart, during a gripping of the mouthpiece.

4. The mouthpiece of claim 1, wherein the sensing arrangement comprises a motion sensor configured to generate a measurement of lateral motion of the mouthpiece as the upper and lower jaws come together, and/or move apart, during a gripping of the mouthpiece.

5. The mouthpiece of claim 1, wherein the one or more mouth contacting elements comprise one or more sensing elements for the sensing arrangement, each sensing element being configured to sense a mechanical property of the gripping of the mount by the upper and lower jaws.

6. The mouthpiece of claim 5, wherein each sensing element comprises a conductive element configured to act as both a sensing element and a bristle for cleaning the teeth and/or the gum of the subject.

7. The mouthpiece of claim 1, further comprising an electromyography electrode arrangement configured to provide one or more signals that respond to electrical activity in one or more muscles of the jaw, for performing electromyography sensing.

8. The mouthpiece of claim 7, wherein the one or more mouth contacting elements comprise one or more brushing elements configured to brush teeth and/or gums of the subject, wherein the one or more brushing elements are further configured to function as one or more electrode elements for the electromyography electrode arrangement.

9. The mouthpiece of claim 1, wherein the one or more mouth contacting elements comprise one or more brushing elements for brushing or cleaning at least one gum or tooth of the subject.

10. The mouthpiece of claim 1, wherein the one or more mouth contacting elements comprises:

a tooth alignment device configured to align or realign a position of a tooth of the subject.

11. A mouthpiece system comprising:
the mouthpiece of claim 1; and
a processing arrangement configured to:
   receive, from the sensing arrangement of the mouthpiece, the one or more measurements of the mechanical properties of the gripping; and
   process the received one or more measurements to generate an indicator that indicates whether or not there are one or more abnormalities in the upper and/or lower jaws of the subject.

12. The mouthpiece system of claim 11, further comprising a memory configured to iteratively store the one or more measurements obtained by the sensing arrangement, to thereby form stored measurements;
wherein the processing arrangement is configured to process the received one or more measurements and the stored one or more measurements to generate the indicator.

\* \* \* \* \*